United States Patent
Mohajer

(10) Patent No.: US 8,838,206 B2
(45) Date of Patent: Sep. 16, 2014

(54) VERESS NEEDLE WITH ILLUMINATED TIP AND CAVITY PENETRATION INDICATOR

(76) Inventor: Reza S. Mohajer, Encino, CA (US)

( * ) Notice: Subject to any disclaimer, the term of this patent is extended or adjusted under 35 U.S.C. 154(b) by 0 days.

(21) Appl. No.: 13/173,981

(22) Filed: Jun. 30, 2011

(65) Prior Publication Data

US 2012/0004535 A1    Jan. 5, 2012

Related U.S. Application Data

(60) Provisional application No. 61/360,254, filed on Jun. 30, 2010.

(51) Int. Cl.
| | |
|---|---|
| *A61B 5/05* | (2006.01) |
| *A61N 1/30* | (2006.01) |
| *A61M 5/178* | (2006.01) |
| *A61M 5/32* | (2006.01) |
| *A61B 17/34* | (2006.01) |
| *A61B 19/00* | (2006.01) |

(52) U.S. Cl.
CPC ....... *A61B 17/3474* (2013.01); *A61B 2019/521* (2013.01); *A61B 2019/4857* (2013.01)
USPC ........ 600/424; 604/19; 604/158; 604/164.01; 604/272; 606/185

(58) Field of Classification Search
USPC .......... 600/424, 476, 473; 606/144, 148, 185; 604/158, 19, 136, 164.01, 272
See application file for complete search history.

(56) References Cited

U.S. PATENT DOCUMENTS

| | | | |
|---|---|---|---|
| 2,743,119 A | 4/1956 | Covert et al. | |
| 2,766,082 A | 10/1956 | Ritchey | |
| 3,994,287 A | 11/1976 | Turp et al. | |
| 3,995,868 A | 12/1976 | Smith | |
| 4,177,814 A | 12/1979 | Knepshield et al. | |
| 5,112,321 A | 5/1992 | Hiltebrandt | |
| 5,139,485 A * | 8/1992 | Smith et al. | 604/158 |
| 5,147,316 A | 9/1992 | Castillenti | |
| 5,167,636 A | 12/1992 | Clement | |
| 5,421,821 A * | 6/1995 | Janicki et al. | 604/26 |

(Continued)

OTHER PUBLICATIONS

Zakherah, Direct Trocar Versus Veress Needle Entry for Laparoscopy: A Randomized Clinical Trial, Obstetrical & Gynecological Survey, May 2010, pp. 307-308, vol. 65 Issue 5.

*Primary Examiner* — Katherine Fernandez
(74) *Attorney, Agent, or Firm* — Gifford, Krass, Sprinkle, Anderson & Citkowski, P.C.

(57) ABSTRACT

A Veress needle assembly comprises an outer steel tube with a sharpened tip at the distal end surrounding an inner rod having a blunt distal end. The proximal end of the inner rod is spring biased towards a position in which its distal end extends beyond the distal end of the outer stainless steel tube so that while piercing the wall of a body cavity the inner rod is forced upwardly against the spring bias to allow the sharpened end of the outer tube to extend into a cutting position. An indicator light supported on the proximal end of the assembly is controlled by a switch which is in a first position when the outer tube is passing through the wall of the body cavity and a second position when the outer tube enters the body cavity behind the wall, allowing the rod to move beyond the distal end of the outer tube, thereby changing the illumination of the light source so that the operator is signaled that the Veress needle has passed into the body cavity.

4 Claims, 2 Drawing Sheets

(56) References Cited

U.S. PATENT DOCUMENTS

| | | | |
|---|---|---|---|
| 5,429,636 A * | 7/1995 | Shikhman et al. | 606/41 |
| 5,437,646 A | 8/1995 | Hunt et al. | |
| 5,626,590 A | 5/1997 | Wilk | |
| 5,727,770 A | 3/1998 | Dennis | |
| 5,873,297 A | 2/1999 | Stojic | |
| 6,387,043 B1 * | 5/2002 | Yoon | 600/109 |
| 7,309,341 B2 * | 12/2007 | Ortiz et al. | 606/153 |
| 7,344,547 B2 | 3/2008 | Piskun | |
| 8,197,443 B2 * | 6/2012 | Sundar et al. | 604/121 |
| 2006/0268570 A1 * | 11/2006 | Vayser et al. | 362/572 |
| 2007/0270653 A1 * | 11/2007 | Vayser et al. | 600/182 |
| 2008/0091144 A1 | 4/2008 | Moran et al. | |
| 2008/0262302 A1 * | 10/2008 | Azarbarzin et al. | 600/114 |
| 2010/0268162 A1 | 10/2010 | Shelton, IV et al. | |
| 2010/0274193 A1 | 10/2010 | Patton et al. | |
| 2011/0028796 A1 | 2/2011 | Blinman et al. | |

\* cited by examiner

VERESS NEEDLE WITH ILLUMINATED TIP AND CAVITY PENETRATION INDICATOR

CROSS-REFERENCE TO RELATED APPLICATION

This application claims priority of U.S. Provisional Application No. 61/360,254 filed Jun. 30, 2010, the contents of which are incorporated herein by reference.

FIELD OF THE INVENTION

This invention relates to a Veress needle assembly and more particularly to a Veress needle having a cavity penetration indicator at the proximal end, controlled by the relative positions of an outer steel cutting tube and an interior blunt end rod disposed within the cutting tube.

BACKGROUND OF THE INVENTION

In medical practice Veress needles are employed in laparoscopic surgery for penetrating the outer wall of a body cavity for the purpose of insufflation or aspiration of the cavity. Veress needles generally comprise an outer tube, usually formed of stainless steel, having a sharp distal end. An inner rod having a blunt distal end is slidably supported within the outer tube and is spring biased toward extension in the direction of the distal end of the assembly.

To open a body cavity, the needle is pushed against the wall of the cavity so that the blunt tip of the inner rod retracts against the spring bias relative to the outer cutting tube, allowing the sharp end to pierce the wall of the body cavity. Once the outer tube penetrates the body wall, the inner rod is free to move through the body wall so that the blunt end projects beyond the sharp end of the outer tube and protects any internal organs from puncture.

When the needle has penetrated the wall, the surgeon must terminate the application of pressure to protect the internal organs. My pending patent application Ser. No. 12/693,079 discloses a Veress needle assembly including an illumination system for providing light at the distal end of the Veress needle. The inner rod of the Veress needle may be made of a light-conducting plastic which is illuminated through a bright, small illumination source such as an LED, preferably located at the proximal end of the assembly, or by an illumination source disposed at the blunt end of the inner tube which is powered by electrical leads passing through the tube from the proximal end. The illumination source at the distal end of the assembly is usually visible through the cavity wall so that the operator may determine when the distal end of the tube has penetrated the wall. However, in some cases it may be difficult to see the distal end light source from the exterior of the body.

SUMMARY OF THE INVENTION

The present invention is accordingly addressed to a device, preferably a light source, but possibly an audio indicator, which is located at the proximal end of the assembly and is controlled by a switch which detects when the needle has penetrated the cavity wall to energize the light source or audio indicator to alert the physician. This device may be used alone or in combination with the distally located light source of my previous application as an additional safety measure.

In a preferred embodiment of the invention, which will subsequently be disclosed in detail, the switch which detects penetration of the wall cavity is controlled by the relative position of the outer cutting tube and the blunt ended inner rod. As has been noted, once the outer cutter penetrates the cavity, the inner rod is freed of the pressure of the wall cavity and extends in the distal direction relative to the outer cutter to change the condition of the light source at the proximal end. While the light source is preferably deenergized while the cavity is being penetrated and is energized after the cavity has been penetrated, the reverse arrangement could be employed.

While the present invention is preferably used in connection with a Veress needle assembly, it could be employed with a trocar assembly which is typically used to penetrate the wall of a body cavity without means for insufflation or aspiration of the body cavity by the Veress needle.

BRIEF DESCRIPTION OF THE DRAWINGS

Other objectives, advantages, and applications of the present invention will be made apparent by the following detailed description of preferred embodiments of the invention. The description makes reference to the accompanying drawings in which.

DETAILED DESCRIPTION OF THE PREFERRED EMBODIMENT

Figure 1:
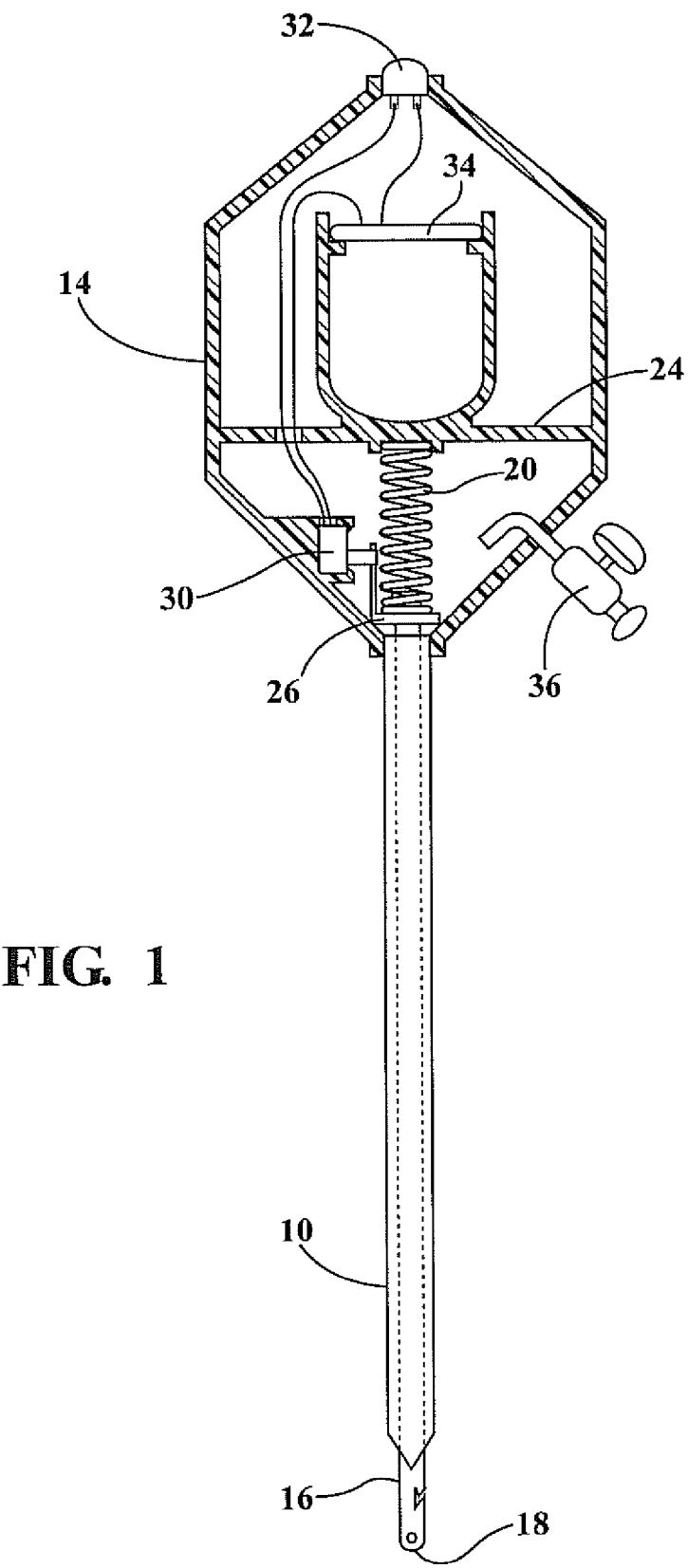
FIG. 1 is a view of a first embodiment of the invention, partially broken away to illustrate details of the invention.

Referring to FIG. 1, the Veress needle assembly comprising a preferred embodiment of the present invention broadly incorporates an outer cutting tube 10, preferably formed of metal or high-strength plastic, and most preferably formed of stainless steel, having a sharpened distal end 12 used to puncture a hole in the body wall of a cavity during performance of laparoscopic surgery or the like or to cut into other body tissues or organs for the purpose of aspirating fluid from the tissues of these organs. The proximal end of the tube 10 is connected to a handle or housing 14.

The tube 10 surrounds an inner rod 16 having a blunt distal end 18. The rod end 18 may be simply rounded or may have a crochet suture hook and hole for the purpose of assisting in performing sutures of the incision formed by the outer tube 10 after termination of a process performed by the Veress needle. The rod 16 freely slides within the outer tube 10 and has its upper end within the housing 14 where it is biased toward the distal end of the assembly by a coil spring 20. The spring 20 wraps around the proximal end of the rod 16 and biases the blunt end 18 of the rod 16 to extend beyond the cutting edge 12 of the tube 10. The lower end of the spring bears against a stop plate 26 affixed near the upper end of the rod.

When the assembly is pressed against the outer surface of a body wall so that the blunt end 18 is pressed upwardly, lifting the stop plate 26 against the bias of the spring 20, the motion of the stop plate 26 throws a switch 30. The switch 30 is connected in serial relationship with an LED light source 32 supported at the proximal end of the housing 14 and to a coin type battery 34. When the rod 16 lifts with respect to the tube 10, the LED light source 32 may either be energized or alternatively deenergized. In either arrangement the surgeon using the Veress needle assembly is signaled that the sharpened end 12 is bearing against the outer wall of the cavity and forming an incision in the cavity. When the cutter end 12 of the tube 10 passes through the wall, reaching the inner cavity, the rod 16 is free to move in the distal direction, into the cavity thus changing the position of the switch 30 and providing an indication to the surgeon or other operator that the cutting end has passed through the cavity and pressure should be released. At that point an insufflation/aspiration connector 34 having a valve 36 may be connected to a source of pressure so as to insufflate the cavity or vacuum so as to aspirate the cavity.

The inventive assembly may also be used to aspirate body tissues or organs such as the heart. If a crochet suture hook and hole is provided at the distal end of the inner rod 18, it may also be used in aid of a suture to close the cavity in the body wall after the operation has been performed.

Figure 2:
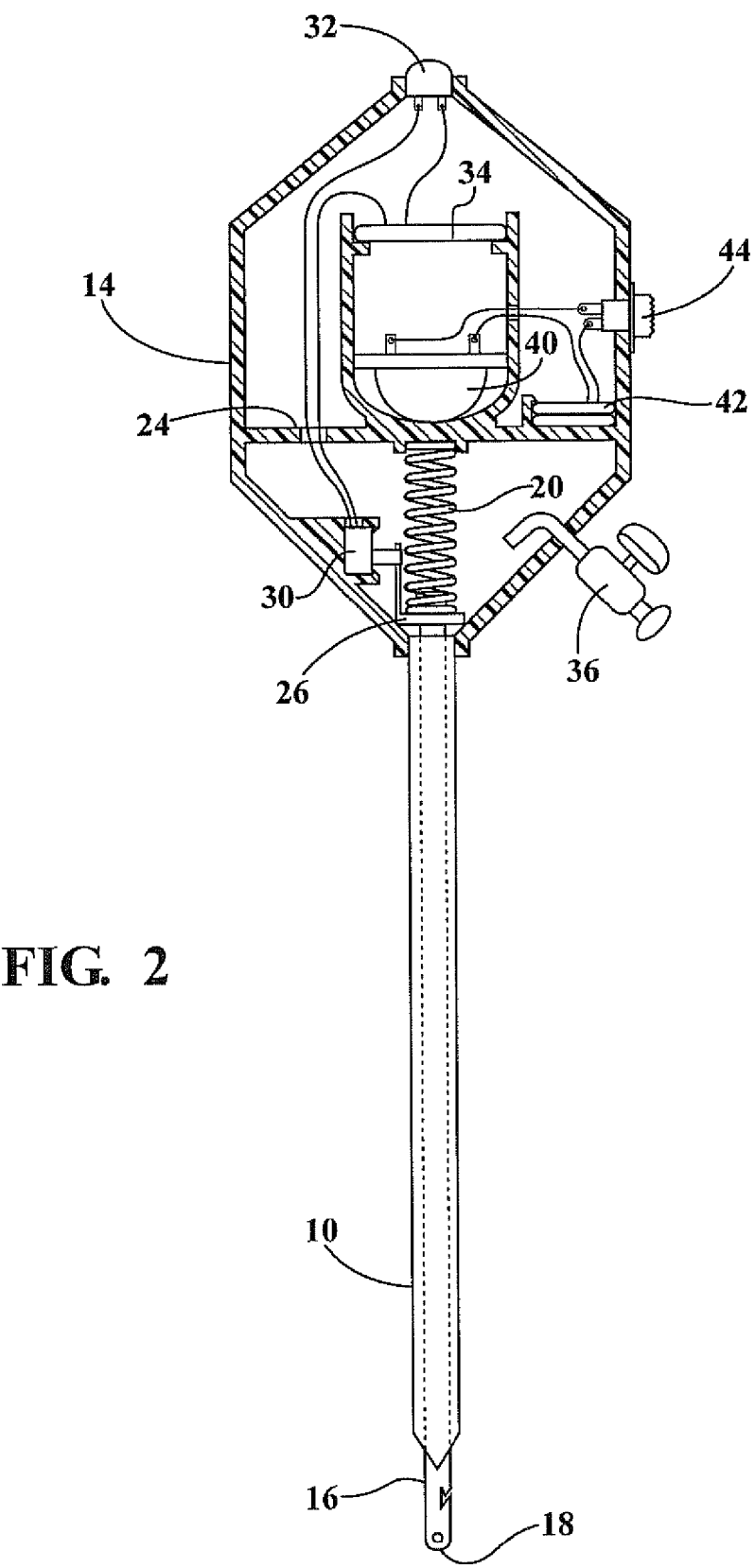
FIG. 2 is an alternative embodiment of the invention additionally incorporating an illumination source at the tip of the blunt ended rod of the Veress needle.

FIG. 2 illustrates an alternative embodiment of the present invention, which differs in only two particular points. First, the inner rod 16 is formed of a clear, light-conductive plastic, preferably Lucite or the like. Second, another light source which may also be an LED, denominated 40, may be disposed within the housing 14. The LED 40 is powered by a battery 42 and controlled by a switch 44. The operator manually operates the switch 44 to energize the light source 40 before piercing the body cavity with the Veress needle assembly. The light produced by the LED 40 is carried to the distal end 18 of the rod 16 so as to provide a light source at the distal end. In many operations the light produced at the distal end will be visible to the surgeon through the body wall so that the surgeon can determine when the body wall has been pierced and where the distal end 18 of the rod 16 is located within the body cavity.

Having thus described our invention, I claim:

1. A Veress needle assembly having a proximal end and a distal end used by a surgeon in piercing a wall of a body cavity, comprising:
    a housing enclosing the proximal end of the assembly;
    an outer tube having proximal and distal ends with the proximal end fixed to and extending from the housing toward the distal end of the assembly, having a sharpened tip at the distal end of the assembly surrounding and slidably supporting an inner rod having a proximal end and a blunt distal end, the proximal end of the inner rod being biased by a spring toward a position in which the blunt distal end of the inner rod extends beyond the distal end of the outer tube so that while piercing the wall of a body cavity the inner rod is forced against the spring bias to allow the sharpened tip of the outer tube to extend beyond the blunt distal end of the inner rod into a cutting position;
    an electrical battery supported within the housing;
    an electric switch supported within the housing; and
    an electrically powered light supported within the housing and connected in serial relationship with the switch and battery, and wherein the switch is connected to the proximal end of the inner rod so that motion of the inner rod controls a position of the switch, wherein said switch is configured to be in a first position when the outer tube is passing through the wall of the body cavity and the inner rod is retracted toward the proximal end of the outer tube, and in a second position when the outer tube enters the body cavity beyond the wall, allowing the distal end of the inner rod to extend under spring bias beyond the distal end of the outer tube,
    wherein the switch is further configured to change a condition of the light based on the position of the switch, and
    wherein said change in the condition of the light is for providing a signal to the surgeon that the outer tube has passed into the body cavity.

2. The Veress needle assembly of claim 1 wherein the bias on the inner rod is created by a compression spring.

3. The Veress needle assembly of claim 2 wherein the compression spring surrounds the proximal end of the inner rod.

4. The Veress needle assembly of claim 1 wherein a stop member is connected to the proximal end of inner rod to limit the extension of the inner rod with respect to the outer tube and the position of the switch is controlled by the position of the stop member.

\* \* \* \* \*